United States Patent

Corbeil

[11] Patent Number: 6,009,869
[45] Date of Patent: Jan. 4, 2000

[54] SUPERSONIC NOZZLE NEBULIZER

[75] Inventor: Scott Corbeil, Nashua, N.H.

[73] Assignee: Allegiance Corporation, McGaw Park, Ill.

[21] Appl. No.: 08/999,013

[22] Filed: Dec. 29, 1997

[51] Int. Cl.$^7$ .................................................. A61M 11/00
[52] U.S. Cl. ........................... 128/200.21; 128/200.14; 128/200.18; 128/203.12; 128/204.25
[58] Field of Search ................................ 239/318, 310, 239/424, 433, 434, 8, 311, 316, 337, 338, 340, 343, 344; 128/200.14, 200.18, 200.21, 203.12, 203.15, 203.22, 204.24, 204.25; 241/DIG. 65

[56] References Cited

U.S. PATENT DOCUMENTS

| | | |
|---|---|---|
| 596,800 | 5/1950 | Johnstone . |
| 1,554,219 | 9/1925 | Kitchen ............................ 128/200.22 |
| 2,062,507 | 12/1936 | Ray-Engleheart . |
| 2,175,160 | 10/1939 | Zobel et al. . |
| 2,297,726 | 10/1942 | Stephanoff . |
| 2,720,203 | 10/1955 | Burns et al. . |
| 2,920,579 | 1/1960 | Grimm . |
| 2,980,033 | 4/1961 | Waddington et al. . |
| 3,537,449 | 11/1970 | Foxwell ............................ 128/204.24 |
| 3,580,249 | 5/1971 | Takaoka ............................ 128/200.14 |
| 3,622,079 | 11/1971 | Greenwood ............................ 239/426 |
| 3,744,722 | 7/1973 | Burns . |
| 3,770,209 | 11/1973 | Wilcox . |
| 4,134,547 | 1/1979 | Gamst . |
| 4,231,973 | 11/1980 | Young et al. ............................ 261/78 |
| 4,268,460 | 5/1981 | Boiarski et al. ............................ 261/1 |
| 4,746,067 | 5/1988 | Svoboda ............................ 239/338 |
| 4,793,556 | 12/1988 | Sharp ............................ 239/418 |
| 4,813,611 | 3/1989 | Fontana . |
| 5,249,740 | 10/1993 | Serra Tosio et al. . |
| 5,287,847 | 2/1994 | Piper et al. . |
| 5,297,543 | 3/1994 | Larson et al. . |
| 5,312,046 | 5/1994 | Knoch et al. ............................ 239/338 |
| 5,337,740 | 8/1994 | Armstrong et al. . |
| 5,355,872 | 10/1994 | Riggs et al. . |
| 5,458,135 | 10/1995 | Patton et al. ............................ 128/200.14 |
| 5,474,059 | 12/1995 | Cooper ............................ 128/200.22 |
| 5,483,953 | 1/1996 | Cooper ............................ 128/200.22 |
| 5,676,130 | 10/1997 | Gupte et al. ............................ 128/203.19 |
| 5,697,361 | 12/1997 | Smith ............................ 128/204.25 |
| 5,775,320 | 7/1998 | Patton et al. ............................ 128/200.14 |
| 5,823,434 | 10/1998 | Cooper ............................ 239/102.2 |

FOREIGN PATENT DOCUMENTS

| | | |
|---|---|---|
| 548068 | 9/1956 | Italy . |
| 52-74109 | 12/1975 | Japan . |

OTHER PUBLICATIONS

Nerbrink et al. (1994) Journal of Aerosol Medicine 7:259–276.

Primary Examiner—John G. Weiss
Assistant Examiner—Joseph F. Weiss, Jr.
Attorney, Agent, or Firm—Swanson & Bratschun LLC

[57] ABSTRACT

A nebulizer for entraining liquid in a flow of carrier gas from a carrier gas source at a select pressure includes a nozzle defining a passage which is circular in cross section and includes a converging section, a throat and a uniformly diverging section, all of which are coaxial and serially connected. The nozzle has an inlet at the mouth of the converging section and an outlet defining a primary orifice at the mouth of the diverging section. The inlet is connectable in fluid communication with the pressurized carrier gas source. The nebulizer further includes a reservoir for the liquid to be entrained and a conduit for conveying a liquid in the reservoir between the reservoir and the primary orifice. The conduit further includes a jacket spaced from and enveloping the primary orifice defining a liquid chamber about the primary orifice. The jacket has a secondary orifice spaced from and coaxial with the primary orifice. A method of entraining a liquid in a flow of carrier gas for delivery to a patient utilizes the nozzle described above to accelerate a carrier gas to a supersonic velocity. A liquid is delivered to the primary orifice and sheared by the supersonic carrier gas.

18 Claims, 2 Drawing Sheets

SUPERSONIC NOZZLE NEBULIZER

BACKGROUND OF THE INVENTION

1. Technical Field

The present invention is directed toward an apparatus and method for entraining particles in a gas stream, more particularly toward a nebulizer having a nozzle generating supersonic velocities of carrier gas for entraining liquid particles in the carrier gas.

2. Background Art

A variety of compressed-gas operated nebulizers have been used for inhalation delivery of aerosols containing small particles of liquid medication to the conductive airways of the lung and the alveoli. Aerosols as used herein are relatively stable suspensions of finely divided liquid particles or solid particles in a gaseous medium, usually air or oxygen enriched air. When inhaled, aerosol particles are deposited by contact upon the various surfaces of the respiratory tract, with the goal being to deposit as great a percentage as possible of the liquid or solid particles for the desired therapeutic action or planned diagnostic activity. Inhalable aerosols are those consisting of particles smaller than 10 micrometers in equivalent diameter.

Medications deposited in the lung can readily enter the blood for action throughout the body because of the high permeability of the lung and the copious blood flow. Other medications can directly influence the efficiency of the oxygen/$CO_2$ exchange of the lungs. Other types of aerosol particles deposited in the lung can be used as tracers of air flow or indicators of lung responses and are therefore useful as a valuable diagnostic tool.

Medical nebulizers are designed to convert water or aqueous solutions or colloidal suspensions to aerosols of fine, inhalable liquid particles that can enter the lungs of a patient during inhalation and deposit on the desired surface of the respiratory airway. One of the critical factors determining where the therapeutic aerosolized particles will be deposited within the pulmonary tree is the Mass Medium Aerosol Diameter ("MMAD"). Generally speaking, as the MMAD decreases, the site of deposition becomes more distal, up to a certain point where further decreases in the MMAD will result in particles being exhaled back out of the airway. In most medial applications, particles in the respiratory range have MMAD of 0.5–5 microns. For application of bronchodialators, MMAD ranges are preferably between 1.8–2.5 microns. For most aerosol AIDS therapies, the desired MMAD is in the range of 1 micron.

Typical pneumatic medical nebulizers feature a converging nozzle having an inlet and an outlet, with the outlet defining a primary orifice. Gas is provided to the nozzle inlet under pressure and accelerated by the converging nozzle to a subsonic, or at best, sonic velocity at the primary orifice. The high velocity of the air at the primary orifice creates a negative pressure which is used to draw liquid from a reservoir into contact with the high velocity carrier gas stream. As liquid is drawn into contact with the gas stream, it is sheared into small particles. The resulting entrained liquid/carrier gas flow is then impinged upon an impingement baffle to collect particles of greater than a select size. This type of nebulizer structure is well known in the art and representative examples include Piper, U.S. Pat. No. 5,287,847, Riggs, U.S. Pat. No. 5,355,872 and Burns, U.S. Pat. No. 3,744,722.

The nebulizers described above typically provide a fairly wide distribution of MMAD. Thus, such nebulizers do not lead to efficient delivery of aerosols of a particular MMAD. Illustrations of particle size distributions for a number of commercially available nebulizers are included in FIG. 6 of Nerbrink et al. (1994) J. Aerosol Med. 7:259. This figure illustrates relatively broad distributions, typically in ranges of 1–10 microns, with MMAD in the range of 3–9 microns. In those instances where delivery of a large percentage of particles of a select MMAD is desired, particularly a small MMAD in the range of 1 micron, such nebulizers are not well suited.

The energy of accelerated carrier gas flows in pneumatic nebulizers are typically used in two ways. First, the energy creates a low pressure zone by the increased velocity of the carrier gas which is used to draw a column of medication to be aerosolized into the flow stream. Second, once the medication has reached the flow stream, energy is expended in the shearing of the fluid into particles and carrying the suspension to the impact baffle. Higher velocity carrier gas flows, such as super sonic carrier gas flows, would make more energy available for both the shearing process as well as a greater pressure drop for drawing liquid medications into the flow stream. The increased energy for shearing should result in a larger percentage of small MMAD particles whereas the greater pressure drop will enable a higher quantity of liquid to be entrained in the carrier gas. This phenomenon is discussed in Nerbrink et al. (1994) J. Aerosol Med. 7:259.

Converging/diverging nozzles (also known as Delaval type nozzles) are known for accelerating the flow of compressed gas to a supersonic speed. For example, Fontana, U.S. Pat. No. 4,813,611, discloses a converging/diverging compressed air nozzle useful in tools for dislodging earth for excavation. Stephanoff, U.S. Pat. No. 2,297,726, teaches a converging/diverging type nozzle for accelerating a carrier gas to supersonic velocity for the purpose of drying atomized particles. Stephanoff teaches that the liquid is introduced to the throat of the converging/diverging nozzle, as illustrated in FIG. 3, or within the diverging section, as illustrated in FIG. 4. Serra Tosio, U.S. Pat. No. 5,249,740, is directed to an apparatus for humidifying instrumentation and also discloses a converging/diverging nozzle wherein liquid to be entrained is introduced into the throat of the nozzle. None of these references teach the use of a converging/diverging nozzle for creating supersonic carrier gas flows in a medical nebulizer. Moreover, in practice, the mass of the liquid introduced in the throat of the converging/diverging nozzle has been found to prevent the combination of carrier gas and entrained liquid from being accelerated to supersonic velocities. In addition, introducing liquid to the throat to the converging/diverging nozzle does not subject the liquid to the highest velocity (and therefore highest shearing energy) gas flow.

The present invention is directed to overcoming one or more of the problems discussed above.

SUMMARY OF THE INVENTION

A first aspect of the present invention is a medical nebulizer for entraining liquid in a flow of carrier gas from a carrier gas source at a select pressure. The medical nebulizer comprises a nozzle defining a passage which is circular in cross-section and includes a converging section, a throat and a uniformly diverging section, all of which are coaxial and serially connected. The nozzle has an inlet at the mouth of the converging section and an outlet defining a primary orifice at the mouth of the diverging section. The inlet is connectable in fluid communication with the pressurized carrier gas source. The nebulizer further includes a reservoir for the liquid to be entrained and a conduit for conveying a liquid in the reservoir between the reservoir and the primary orifice. The conduit further includes a jacket spaced from and enveloping the primary orifice, the jacket defining a liquid chamber about the primary orifice. The jacket has a secondary orifice spaced from and coaxial with the primary orifice. The reservoir preferably lies below the primary orifice and with the nozzle inlet in fluid communication with the pressurized carrier gas source, liquid is caused to flow from the reservoir to the primary orifice by a vacuum generated by the velocity of the carrier gas exiting the primary orifice.

Another aspect of the present invention is a method of entraining a liquid in a flow of carrier gas for delivery to a patient. A carrier gas flow at between about 35–55 psig and 2–15 liters per minute is provided. The carrier gas flow is accelerated to a supersonic velocity using a nozzle defining a passage which is circular in cross-section and includes a converging section, a throat and a uniformly diverging section all being coaxial and serially connected. The nozzle has an inlet at the mouth of the converging section and an outlet defining a primary orifice at the mouth of the diverging section. A flow of liquid to be entrained is delivered to the primary orifice. The flow of liquid is sheared by the supersonic velocity carrier gas to entrain particles of liquid in the carrier gas. The flow of carrier gas and entrained liquid particles are delivered to the patient. In a preferred embodiment, the primary orifice has a diameter of between 0.016 and 0.040 inches and the diverging section has an interior apex angle that does not exceed 7°.

The nebulizer including the supersonic nozzle of the present invention provides a high energy flow of carrier gas capable of shearing a liquid to be entrained into minute particles having a narrow MMAD distribution and can entrain greater volumes of liquid than using conventional subsonic nebulizer nozzles. FIG. 1 is a graph of an idealized particle size distribution that it is hoped results from the invention, although no measurements have been taken to date. These advantages can be provided with a nozzle that can be readily manufactured from conventional materials.

DETAILED DESCRIPTION OF THE PREFERRED EMBODIMENT

Figure 2:
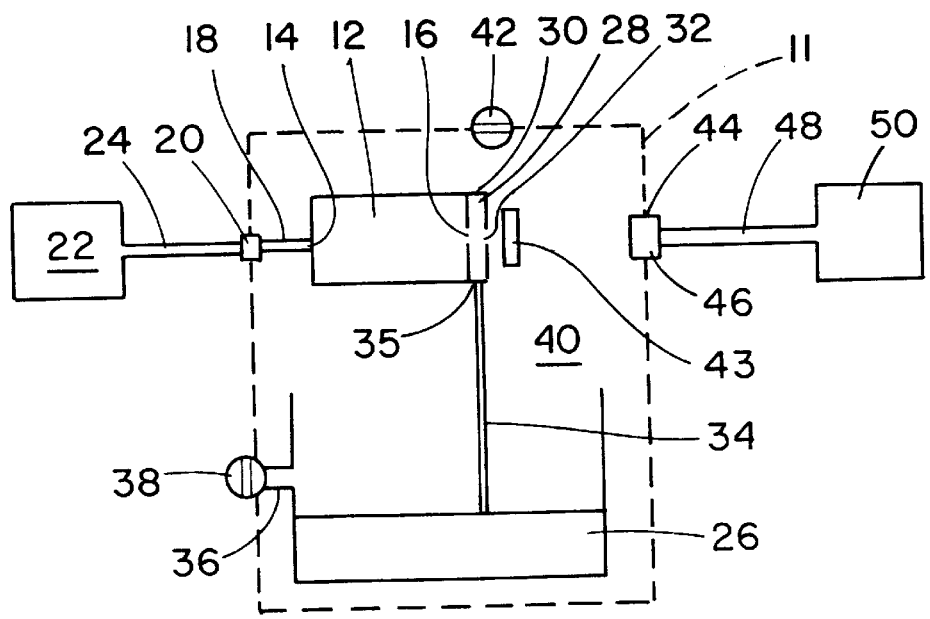
FIG. 2 is a schematic view of a nebulizer including a supersonic nozzle in accordance with the present invention.

FIG. 2 is a schematic representation of a supersonic nozzle nebulizer 10 in accordance with the present invention. The supersonic nozzle nebulizer 10 is contained within a housing represented by the phantom line 11. The supersonic nozzle nebulizer 10 includes a converging/diverging nozzle 12 having an inlet 14 and an outlet or primary orifice 16. A conduit 18 extends from the inlet 14 and terminates at a connector 20 on the housing 11. A source of carrier gas 22 is in fluid communication with the inlet 14 through a tube 24 coupled to the connector 20.

A reservoir 26, which is preferably within the housing 11, is in liquid communication with a liquid chamber 28 defined by a jacket 30 enveloping the primary orifice 16. The jacket 30, as shown in greater detail in FIG. 3, defines a secondary orifice 32 which is coaxial with the primary orifice 16 and of a slightly larger diameter. A fluid supply conduit 34 maintains the liquid reservoir 26 in fluid communication with the liquid chamber 28 by connection to the jacket inlet 35. A liquid inlet 36 including a cover or valve 38 on the housing 11 enables the reservoir 26 to be replenished as needed.

The secondary orifice 32 opens to a mixing chamber 40. A valve 42 extends between the ambient atmosphere and the mixing chamber 40 to allow for the introduction of ambient air into the mixing chamber, as will be described in greater detail below. An impingement baffle 43 is disposed outside the secondary orifice 32. The mixing chamber has an outlet 44 in the housing 11 which includes a conventional connector 46 which enables connection of a tube 48 between the liquid chamber outlet 44 and the airway of a patient 50.

Figure 3:
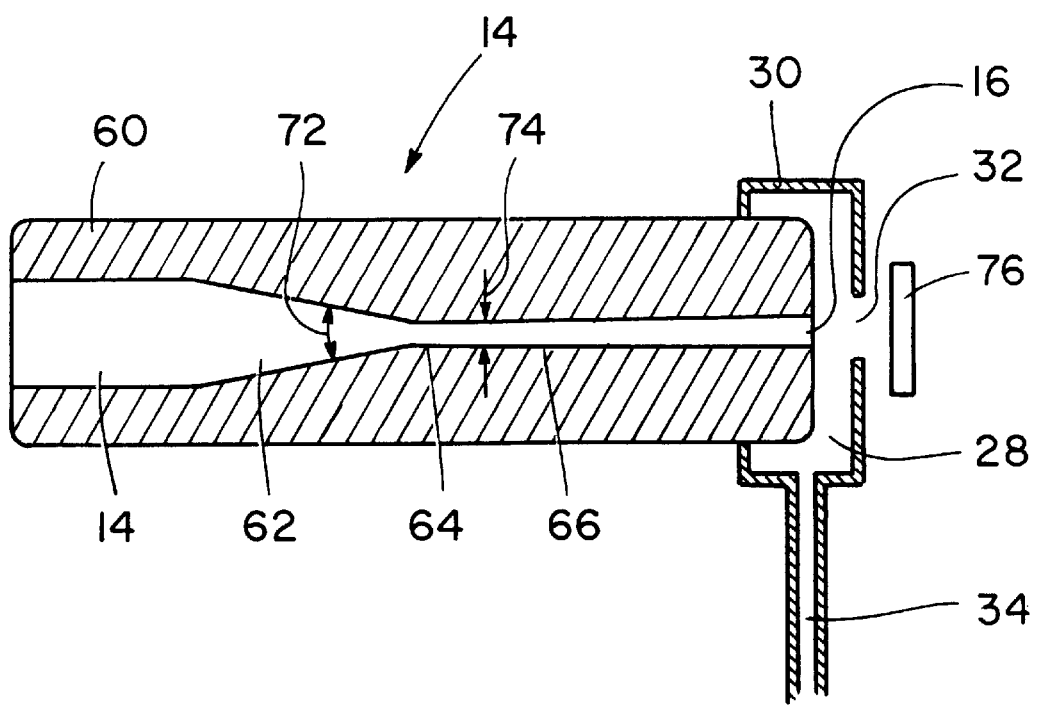
FIG. 3 is a cross-section view of a supersonic nozzle and fluid delivery jacket in accordance with the present invention

The converging/diverging nozzle 12 is shown in greater detail in FIG. 3. The converging/diverging nozzle 12 defines a passage way within a block 60 which is circular in cross-section and includes a uniformly converging section 62, a throat 64 and a uniformly diverging section 66, each of which is coaxial and serially connected. The inlet 14 is at the mouth of the converging section 62. The converging section need only converge at an acute angle to minimize head loss. Modification of the converging section would not necessarily effect production of supersonic velocity flows at the primary orifice 16. The primary orifice 16 is at the mouth of the diverging section 66. The inlet, as illustrated in FIG. 3, may be a cylindrical section. The diameter of the inlet 14 is preferably in a range of 0.050–0.150 inches, although the precise size is not critical to reaching supersonic velocities. The throat preferably has a diameter of between 0.012–0.022 inches. The diverging section 66 has a inner apex angle 74 that does not exceed 7°. The primary orifice has a diameter of between about 0.016–0.040 inches. The critical parameter for determining the Mach number (i.e., supersonic velocity) generated is the ratio of the primary orifice 16 area to the throat 64 area. Table 1 below sets forth a theoretical Mach number (Ma) achieved for various ratios of primary orifice area to throat area, assuming an interior diverging angle of less than 7°.

TABLE 1

| Area of Exit / AreaofThroat | Ma |
| --- | --- |
| 1.047 | 1.25 |
| 1.176 | 1.5 |
| 1.387 | 1.75 |
| 1.688 | 2.0 |
| 2.046 | 2.25 |
| 2.637 | 2.5 |

In a preferred embodiment, the inlet diameter is between about 0.089–0.099 inches, the throat diameter is between about 0.019–0.021 inches and the primary orifice has a diameter between about 0.025–0.027 inches. The interior apex angle of the converging section is not critical, but is preferably an acute angle to reduce head losses to the throat. The interior angle of the diverging section is about 0.63°. The ratio of the exit area to throat area in this preferred embodiment is about 1.625, meaning the theoretical Mach number of an exiting gas supplied at about 50 psig is about 1.28.

Figure 1:
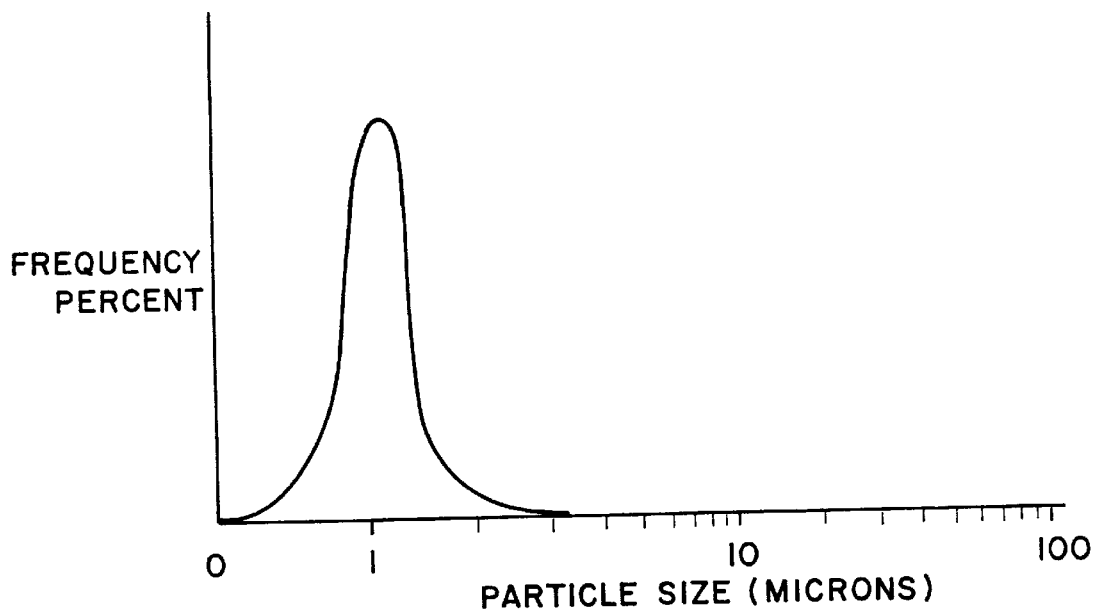
FIG. 1 is a graph of an ideal MMAD distribution of a supersonic nozzle nebulizer in accordance with the present invention.

In use, with the supersonic nebulizer 10 configured as illustrated in FIG. 1, the pressurized carrier gas entering the inlet 14 of the converging/diverging nozzle 12 is accelerated to a supersonic velocity by the time it reaches the primary orifice 16. The carrier gas, typically oxygen, is provided at between about 35–55 psig and a flow rate of 2–15 liters per minute. The high velocity of the carrier gas flow creates a subatmospheric pressure at the primary orifice 16. As a result, a partial vacuum is formed in the liquid chamber 28 which causes liquid from the reservoir 26 to be drawn into the liquid reservoir 28. The liquid surrounds the primary orifice 16 and a substantially even flow of liquid is drawn around the periphery of the primary orifice 16. As the liquid comes in contact with the supersonic velocity of the carrier gas, the liquid is sheared into minute droplets and propelled out the secondary nozzle 32. Substantially all the entrained liquid particles and carrier gas impinge upon the impingement baffle 43. The baffle 43 is spaced so that particles of greater than a select size will stick to the baffle 43 and collect as droplets which are returned to the liquid reservoir 26. Preferably the impingement baffle is about 0.007–0.020 inches from the secondary orifice. Much of the velocity of the carrier gas/entrained liquid particle combination is dissipated in the mixing chamber 40 before the combination exits through the outlet 44 for delivery to the airway of a patient 50 through the tube 48.

In many instances the carrier gas is pure oxygen. It is often desirable to dilute the oxygen concentration in the carrier gas before delivery to the patient airway. The valve 42 is located in close proximity to the secondary orifice 32. The carrier gas/entrained liquid exiting the secondary orifice 32 has a high enough velocity to create a subatmospheric pressure in the vicinity of the valve 42. As a result, ambient air can be drawn into the mixing chamber through the valve 42. The valve 42 can be adjusted to allow mixing with enough ambient air to provide the desired enhanced concentration of the oxygen in the air/entrained liquid leaving the mixing chamber.

The supersonic nozzle nebulizer of the present invention provides carrier gas flows of enhanced kinetic energy that are able to shear liquid particles into consistently small diameters useful for therapeutic and diagnostic applications. The relatively low pressures created by the high velocity carrier gas as it exits the primary orifice enables enhanced quantities of liquid to be delivered to the primary orifice and therefore entrained in the carrier gas stream. These advantages are accomplished by a converging/diverging nozzle which can be readily and inexpensively manufactured out of conventional materials and incorporated in conventional nebulizer designs.

What is claimed is:

1. A nebulizer for entraining a liquid in a flow of a carrier gas from a carrier gas source at a select pressure, the nebulizer comprising:

a nozzle defining a passage which is circular in cross-section and includes a converging section, a throat, and a uniformly diverging section all being coaxial and serially connected, the nozzle having an inlet at a mouth of the converging section and an outlet defining a primary orifice at a mouth of the diverging section, the inlet being connectable and in fluid communication with the carrier gas source at a select pressure;

a reservoir for a non-aerosolized liquid to be entrained; and a conduit for conveying the non-aerosolized liquid in the reservoir between the reservoir and the primary orifice for aerosolization of the liquid by carrier gas exiting the primary orifice.

2. The nebulizer of claim 1 wherein the throat and diverging section are dimensioned relative to one another to produce a supersonic velocity of the carrier gas at the primary orifice.

3. The nebulizer of claim 2 wherein the select pressure is between about 35–55 psig, the throat has a diameter of between about 0.012 and 0.022 inches, the primary orifice has a diameter of between about 0.016 and 0.040 inches, and the diverging section has an interior apex angle that does not exceed 7 degrees.

4. The nebulizer of claim 2 wherein the select pressure is between about 35–55 psig, the throat has a diameter of between about 0.019 and 0.021 inches, the primary orifice has a diameter of between about 0.025 and 0.027 inches, and the diverging section has an interior apex angle that does not exceed 7°.

5. The nebulizer of claim 1 wherein the conduit further comprises:

a jacket spaced from and enveloping the primary orifice defining a liquid chamber about the primary orifice, the jacket having a secondary orifice spaced from and coaxial with the primary orifice.

6. The nebulizer of claim 5 further comprising an impingement baffle spaced from the secondary orifice a distance whereby substantially the entire flow of carrier gas and entrained liquid strikes the impingement baffle, the impingement baffle collecting particles of greater than a select size while allowing substantially all the particles less than the select size to remain entrained in the carrier gas.

7. The nebulizer of claim 1 wherein the reservoir lies below the primary orifice and with the nozzle inlet in fluid communication with the pressurized carrier gas source, the non-aerosolized liquid is caused to flow from the reservoir to the primary orifice by a vacuum generated by the velocity of the carrier gas flow exiting the primary orifice.

8. A nebulizer for entraining a liquid in a flow of a carrier gas from a carrier gas source at a select pressure, the nebulizer comprising:

a nozzle defining a passage which is circular in cross-section and includes a uniformly converging section, a throat and a uniformly diverging section all being coaxial and serially connected, the nozzle having an inlet at the mouth of the converging section and an outlet defining a primary orifice at the mouth of the diverging section, the inlet being connectable and in fluid communication with the pressurized gas source;

a reservoir for the liquid to be entrained;

a jacket spaced from and enveloping the primary orifice in liquid tight attachment to the nozzle defining a liquid chamber about the primary orifice, the jacket having a secondary orifice; and a conduit between the reservoir and the jacket inlet for conveying the liquid between the reservoir and the jacket inlet with the nozzle inlet connected in fluid communication with the pressurized gas source.

9. The nebulizer of claim 8 wherein the throat and diverging section are dimensioned relative to one another to produce a supersonic velocity of the carrier gas at the primary orifice.

10. The nebulizer of claim 9 wherein the ratio of the area of the primary orifice to the throat is between about 1.047–2.637 and interior angle of the diverging section is less than 7°.

11. The nebulizer of claim 9 wherein the select pressure is between about 35–55 psig, the throat has a diameter of between about 0.012 and 0.022 inches, the primary orifice has a diameter of between about 0.016 and 0.040 inches, and the diverging section has an interior apex angle that does not exceed 7 degrees.

12. The nebulizer of claim 9 wherein the select pressure is between about 35–55 psig, the throat has a diameter of between about 0.019 and 0.021 inches, the primary orifice has a diameter of between about 0.025 and 0.027 inches, and the diverging section has an interior apex angle that does not exceed 7 degrees.

13. The nebulizer of claim 8 further comprising an impingement baffle spaced from the secondary orifice a distance whereby substantially the entire flow of carrier gas and entrained liquid strikes the impingement baffle, the impingement baffle collecting particles of greater than a select size while allowing substantially all the particles less than the select size to remain entrained in the carrier gas.

14. The nebulizer of claim 10 wherein the converging portion has a length of about 0.174–0.204 inches, the throat has a length of between about 0.028–0.032 inches and the diverging portion has a length of between about 0.307–0.331 inches.

15. A method of entraining a liquid into a flow of carrier gas for delivery to a patient comprising:
   a. providing a carrier gas flow at about 35–55 psig and 2–15 liters per minute;
   b. accelerating the carrier gas flow to a supersonic velocity using a nozzle defining a passage which is circular in cross-section and includes a converging section, a throat and a diverging section all being coaxial and serially connected, the nozzle having an inlet at a mouth of the converging section and an outlet defining a primary orifice at the mouth of the diverging section;
   c. delivering a flow of a non-aerosolized liquid to be entrained to the primary orifice;
   d. shearing the flow of non-aerosolized liquid with the supersonic velocity of the carrier gas to entrain particles of liquid into the carrier gas;
   e. dissipating the velocity of the carrier gas and entrained particles of liquid; and
   f. delivering the flow carrier gas and entrained liquid particulates to the patient.

16. The method of claim 15 further comprising after step d., impinging the carrier gas and entrained liquid particles on an impingement baffle to collect substantially all liquid particles of greater than a select diameter.

17. The method of claim 15 wherein the step c. the flow of non-aerosolized liquid is delivered substantially evenly across the periphery of the primary orifice.

18. The method of claim 15 wherein in step b. the primary orifice has a diameter of between 0.016 and 0.040 inches and the diverging section has an inner apex angle that does not exceed 7 degrees.

* * * * *